United States Patent [19]

Berthold et al.

[11] 4,375,561

[45] Mar. 1, 1983

[54] PROCESS FOR THE PREPARATION OF AROMATIC AMINES

[75] Inventors: Rüdiger Berthold, Bad Soden am Taunus; Werner H. Müller, Eppstein, both of Fed. Rep. of Germany

[73] Assignee: Hoechst Aktiengesellschaft, Frankfurt am Main, Fed. Rep. of Germany

[21] Appl. No.: 318,117

[22] Filed: Nov. 4, 1981

[30] Foreign Application Priority Data

Nov. 6, 1980 [DE] Fed. Rep. of Germany ....... 3041836

[51] Int. Cl.$^3$ .............................................. C07C 85/11
[52] U.S. Cl. .................................................... 564/415
[58] Field of Search ........................................ 564/415

[56] References Cited

U.S. PATENT DOCUMENTS 3,255,248  6/1966  Suessenguth ................... 564/415 X
4,247,479  1/1981  Berthold ....................... 564/415 UX

FOREIGN PATENT DOCUMENTS 2623174  12/1977  Fed. Rep. of Germany ...... 564/415

Primary Examiner—Paul F. Shaver
Attorney, Agent, or Firm—Curtis, Morris & Safford

[57] ABSTRACT

Aromatic amines are obtained from the corresponding cycloaliphatic oximes by heating the oxime to a temperature of from 150° to 350° C. in an ether group containing solvent in the presence of a catalyst containing a noble metal of the 8th auxiliary group of the Periodic Table of Elements. The solvent is preferably an aliphatic ether, especially a lower dialkyl ether of a polyethyleneglycol.

8 Claims, No Drawings

PROCESS FOR THE PREPARATION OF AROMATIC AMINES

It is known that primary aromatic amines can be prepared from 2-cyclohexenone oximes with the use of agents splitting off water (German Pat. No. 2,654,852). In J. Amer. Chem. Soc. 69 (1947), 1907-1908, there is described how to prepare primary aromatic amines from the corresponding 2-cyclohexenone azines by heating the azines in alkylaromatic compounds, especially triethylbenzene, in the presence of noble metal catalysts. Adaptation of this reaction to 2-cyclohexenone oximes failed however.

Surprisingly, there has now been found that aromatic amines can be prepared from the corresponding cycloaliphatic oximes by heating the oxime to a temperature of from 150° to 350° C. in an ether group containing solvent in the presence of a catalyst containing a noble metal of the 8th auxiliary group of the Periodic Table of Elements. When starting from a cyclohexenone oxime, one mol of water is split off in the process of the invention, when starting from a saturated oxime, catalytic dehydrogenation occurs in addition.

Preferred embodiments of the invention are described in detail as follows.

Suitable starting materials are saturated as well as unsaturated mono- and polynuclear oximes which may carry inert substituents. Of course, these substituents must be arranged in such a manner that aromatization of the molecule is possible. Excluded are "bulky" substituents in positions adjacent to the oxime group, because they would hinder or prevent contact of the oxime molecule with the catalyst.

Preferred starting materials are cyclohex-2-en-1-one oximes or the corresponding tetrahydronaphthalen-1-one oximes, because they yield the corresponding primary aromatic amines with a high selectivity. Especially preferred are cyclohex-2-ene oximes of the formula

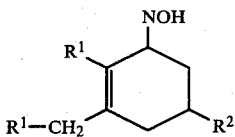

in which $R^1$ and $R^2$ each are hydrogen, lower alkyl or phenyl. The ketones on which they are based are easily obtainable from the corresponding acylacetic esters and aldehydes, for example according to the process of German Offenlegungsschrift No. 2,654,850, and the oximes in turn are easily prepared from these ketones, for example likewise according to the process of German Offenlegungsschrift No. 2,654,851.

Owing to the fact that the process of the invention is a reaction in a heterogeneous system, it is advantageous to care for constant good intermixing, which is ensured by corresponding agitation or in simple manner by vigorous boiling.

The preferred reaction temperature is in the range of from 180° to 260° C., because in this range the reaction proceeds rapidly and generally with high selectivity. Depending on the kind of solvent used, the reaction is carried out under a pressure of from 0.001 to 100, especially 0.01 to 20, bar; advantageously, pressure and temperature are adjusted in such a manner that sufficient liquid phase is present and the intended reaction temperature is maintained.

Suitable solvents are in principle all ethers. Preferred are aliphatic ethers, that is, those which contain at least one aliphatic group. Ethers having a boiling point of at least about 80° C. are preferably used, because in the case of lower boiling ethers a relatively high pressure is required in order to attain a sufficiently high reaction temperature at which the reaction is completed within an acceptable period of time.

Suitable are high-boiling dialkyl ethers, for example di-n-butyl ether, alkylaryl ethers such as anisol and phenetol, especially polyethers derived from ethyleneglycol and/or propyleneglycol. Suitable polyethers of this type are in the most simple case lower dialkyl ethers of ethyleneglycol or propyleneglycol, preferably, however, lower dialkyl ethers of polyglycols such as ethylenedi-, -tri- or -tetraglycol, or of higher polyglycols are used, furthermore monoaryl ethers such as addition products of ethylene oxide to alkylphenols such as nonylphenol or tributylphenol, the free hydroxy group of which is etherified with lower alkanols. Suitable ethers are furthermore higher polyglycols having free terminal hydroxy groups; preferred, however, are their lower dialkyl ethers having up to 6 carbon atoms in the ether groups, especially the methyl or ethyl ethers.

Advantageously, an ether is chosen the boiling point of which under atmospheric pressure is in the preferred temperature range of from 180° to 260° C., because this solvent allows operations without pressure, and the reaction proceeds under reflux conditions in an especially rapid and selective manner. Depending on the reaction conditions, the boiling point of the solvent can be chosen in such a manner that on work-up the amine is in the distillation sump or in the distillate. An advantageous embodiment of the invention is the following: a high-boiling ether is used and the amine is distilled off to that extent to which it is formed, optionally under reduced pressure, so that merely a small amount of solvent is required. When an ether having a lower boiling point than the amine formed is used, the solvent can be distilled off continuously and recycled to the process in order to save solvent, while the amine is discharged from the sump. These processes can be carried out in a fully continuous manner, too. For example, a solution of the oxime in the same solvent which is used for suspending the catalyst, or the molten oxime is continuously introduced into the reactor via a preheater, while simultaneously a corresponding amount of reaction mixture containing the amine formed is discharged. The catalyst is maintained in the reactor for example by means of a frit, or recycled to the reactor after separation for example by means of a decanter. After separation by distillation from the amine formed, the solvent is reused for dissolving fresh oxime.

Alternatively, the oxime can be added in a form dissolved in a low-boiling solvent which is continuously distilled off during the reaction. As such low-boiling solvent for the oxime not only ethers, but also other sufficiently inert solvents may be used, for example lower alkanols such as isopropanol.

In addition to the kind of solvent, its amount, too, has a certain influence on the reaction, since the yield decreases with increasing concentration of the oxime used and the amine formed. In principle, the yields are the higher the lower the concentration is. For economic reasons, an oxime and amine concentration in the reaction mixture of up to about 30 weight %, preferably up to about 15%, relative to the weight of the solvent, is chosen.

In order to keep the oxime concentration as low as possible, the speed of the oxime addition is advantageously adjusted to the throughput capacity of the catalyst used, which can be easily determined by a simple preliminary test.

The catalysts are either skeleton or carrier catalysts containing as active metal advantageously ruthenium, rhodium, iridium, but especially palladium or platinum, or several of these metals. Suitable carriers for the catalysts are generally carbon, silicium dioxide, aluminum oxide, aluminum silicates, mixed oxides such as chromium oxide/aluminum oxide, or spinels, barium sulfate, or mineral carriers such as zeolites. The concentration of the noble metal on the carrier is generally from 0.05 to 10, preferably 0.2 to 5, and especially 0.5 to 2.5%, relative to the weight of the carrier.

When commercial carrier catalysts are employed, a catalyst particle size of from about 0.01 to 5, preferably 0.05 to 1, mm is chosen. Depending on the solvent and the catalyst, the reaction suspension can contain from 0.1 to 40% of carrier catalyst, relative to the weight of the liquid reaction medium. Preferred are from 1 to 30%, relative to the weight of the solvent.

The catalyst activity decreases slowly in the course of the reaction, and by-products are formed to a corresponding extent. These by-products remain in the residue on separation by distillation of the amine. For separation from the solvent, the distillation residue which has been suction-filtered from the catalyst can be poured onto water, so that the undissolved by-products are eliminated and the aqueous filtrate clarified with carbon is dehydrated by distillation.

The following examples illustrate the invention; percentages being by weight unless otherwise stated.

EXAMPLE 1

A solution of 12 g of 3-methyl-5-propyl-2-cyclohexenone oxime (MW 167) in 100 ml of isopropanol is added dropwise within 4 hours and with thorough agitation to a suspension of 10 g of a catalyst consisting of 5% of Pd on $Al_2O_3$ powder in 100 ml of methylbutyl-diethyleneglycol (b.p. 215° C.) in a 250 ml four-necked flask provided with a small Vigreux column and a descending cooler.

The reaction mixture is heated to an inner temperature of 210° C., and the isopropanol is uniformly distilled off via the column. After having added dropwise the complete amount of oxime, agitation is continued for 30 minutes, and the cooled solution is suction-filtered from the catalyst. 85.5 g of reaction solution are obtained. Gas chromatography analysis gives a content of 11.3% of 3-propyl-5-methylaniline (MW 149), corresponding to 9.66 g=90.0% of theory, and 0.6% (corresponding to 0.51 g=5.0% of theory), of the diaryl amine of the formula

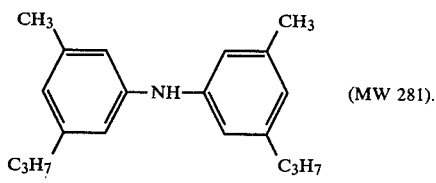

(MW 281).

By fractionation of the catalyst-free reaction solution, 3-propyl-5-methylaniline, b.p. 106° C. at 1.2 mbar, is obtained.

EXAMPLE 2

In the manner as described in Example 1, 15 g (108 mmols) of 3,5-dimethyl-2-cyclohexenone oxime, dissolved in 100 ml of isopropanol, are reacted at 175°–180° C. in the presence of a Pd catalyst (5% of Pd on carbon, Messrs. Engelhardt) and diethyl-diethyleneglycol (b.p. 178° C.) as solvent.

81 g of solution are obtained containing 15% of xylidine according to gas chromatography. This corresponds to a yield of 12.15 g of sym. m-xylidine=93% of th. Furthermore, 0.6 g of dixylylamine (MW 225) corresponding to 4.9% of theory are obtained. By fractional distillation, sym. m-xylidine having a boiling point of 226°–228° C. is obtained.

In analogous manner, 3-methyl-5-propyl-6-ethylaniline is obtained with a yield of 89% from 2-ethyl-3-propyl-5-methyl-2-cyclohexenone oxime, 1-naphthylamine with a yield of 56% from tetrahydronaphthalene-1-oxime, and 3-methyl-5-phenylaniline with a yield of 84% from 3-methyl-5-phenyl-2-cyclohexenone oxime.

EXAMPLE 3

11.3 g of cyclohexanone oxime (MW 113), dissolved in 100 ml of isopropanol, are added dropwise to a suspension of a Pd/$Al_2O_3$ catalyst in 100 ml of diethyl-diethyleneglycol, as indicated in Example 1. 71.3 g of solution are obtained having a content of 1.7% of aniline (=1.2 g, corresponding to 13% of theory) and 7.8% of diphenylamine (MW 169) (=5.6 g, corresponding to 65.8% of theory).

EXAMPLE 4

50 g of a 2.8% Pd/$Al_2O_3$ catalyst in powder from and 1 l of dimethyl-diethyleneglycol are introduced into a 1.5 liter stainless steel reactor, provided with stirrer, reflux condenser and automatic control of level and pressure. The batch is heated with nitrogen flushing. The automatic pressure control is adjusted to 1.6 bar, so that a reflux temperature of 190° C. results. 100 g per hour of 3,5-dimethyl-2-cyclohexenone oxime, dissolved in 900 g of dimethyl-diethyleneglycol, are pumped in, and simultaneously 1,000 g of reaction product are removed from the reactor via a filter device which keeps the catalyst in the reactor. Gas chromatography analysis of the reaction product gives 7.93% of sym. m-xylidine (91% of theory). After having distilled off the dimethyl-diethyleneglycol, 99.6% strength xylidine distills at b.p. 93° C./12 mbar.

What is claimed is:

1. A process for the preparation of aromatic amines from the corresponding cycloaliphatic oximes, which comprises heating the oxime to a temperature of from 150° to 350° C. in an ether group containing solvent in the presence of a catalyst containing a noble metal of the 8th auxiliary group of the Periodic Table of Elements.

2. A process as claimed in claim 1, wherein the oxime is a cyclohex-2-en-1-one oxime or a tetrahydronaphthalen-1-one oxime.

3. A process as claimed in claim 1, wherein the oxime is a cyclohex-2-ene oxime of the formula

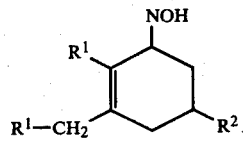

in which $R^1$ and $R^2$ each are hydrogen, lower alkyl or phenyl.

4. A process as claimed in claim 1, wherein the ether group containing solvent is an aliphatic ether.

5. A process as claimed in claim 1, wherein the ether group containing solvent is a lower dialkyl ether of a polyethyleneglycol.

6. A process as claimed in claim 1, wherein the concentration of the oxime in the reaction mixture does not exceed 30 weight %.

7. A process as claimed in claim 1, wherein the concentration of the oxime in the reaction mixture does not exceed 15 weight %, relative to the solvent.

8. A process as claimed in claim 1, wherein the oxime is added to the heated solvent.

* * * * *